United States Patent

Aoki et al.

[11] Patent Number: 4,570,018
[45] Date of Patent: Feb. 11, 1986

[54] FLUOROCYCLOPROPANES

[75] Inventors: Tsutomu Aoki, Osaka; Hiromi Takahashi, Hyogo; Toshiro Konoike; Teruji Tsuji, both of Osaka; Wataru Nagata, Hyogo, all of Japan

[73] Assignee: Shionogi & Co., Ltd., Osaka, Japan

[21] Appl. No.: 610,790

[22] Filed: May 16, 1984

[30] Foreign Application Priority Data

May 31, 1983 [JP] Japan ................................ 58-97629
Jun. 10, 1983 [JP] Japan ............................... 58-104519

[51] Int. Cl.$^4$ .................... C07C 43/192; C07C 87/34; C07C 149/26
[52] U.S. Cl. ............................ 564/1; 260/455 R; 560/219; 560/227; 564/205; 564/209; 564/461; 564/501; 564/504; 568/45; 568/51; 568/56; 568/591; 568/595; 568/596; 568/598; 570/133
[58] Field of Search ................... 570/133; 568/38, 51, 568/56, 669, 670, 591; 564/1, 461

[56] References Cited

U.S. PATENT DOCUMENTS 3,825,606 7/1974 O'Neill et al. ...................... 570/133

OTHER PUBLICATIONS

Nagakura, Isao et al., *Helv. Chem. Acta*, vol. 63 (1980), 1257–1263.
Schlosser, Manfred et al., *Chem. Ber.*, vol. 104 (1971), 1921–1933.

*Primary Examiner*—Natalie Trousof
*Assistant Examiner*—L. Hendriksen
*Attorney, Agent, or Firm*—Wenderoth, Lind & Ponack

[57] ABSTRACT

A novel chemical, fluorochlorocyclopropane (I) of the following formula:

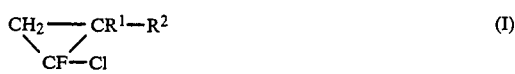

is prepared by the addition of fluorochlorocarbene to the corresponding olefin (II) of the following formula:

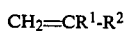

The compound is a useful intermediate for synthesizing some chemicals, e.g., some cephalosporins.
(wherein $R^1$ is hydrogen, halogen, 1 to 8C alkylamino, alkoxy, or alkylthio and
$R^2$ is halogen, 1 to 8C alkylamino, alkoxy, or alkylthio).

5 Claims, No Drawings

FLUOROCYCLOPROPANES

This invention relates to a fluorochlorocyclopropane compound (I) represented by the following formula:

(I)

(wherein $R^1$ is hydrogen, halogen, or 1 to 8C alkylamino, alkoxy, or alkylthio and $R^2$ is halogen or 1 to 8C alkylamino, alkoxy, or alkylthio)

This novel compound (I) is prepared by the addition of fluorochlorocarbene to the corresponding olefin (II) which is converted to carboxymethylthiofluoroacrylate (VIII), a useful intermediate for synthesizing, e.g., new cephalosporins (IX).

Scheme 1

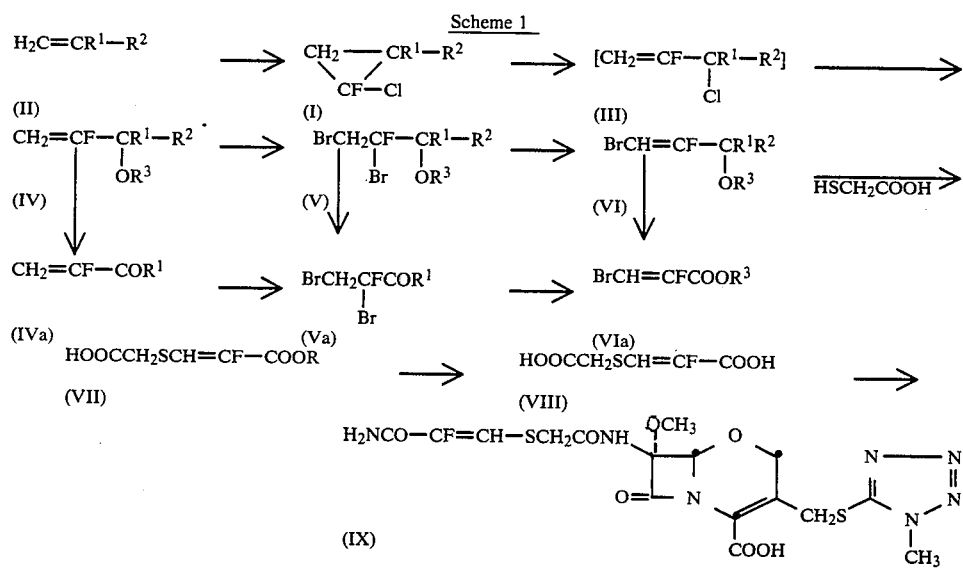

(wherein $R^1$ and $R^2$ each is as defined above and $R^3$ is 1 to 4C alkyl)

Japanese Patent Application No. 128,116/1983 by some of the present inventors et al. describes Compound (VII) prepared from expensive monofluoroacetate. Starting from abundant and inexpensive commodities in the market, the reactions of this invention are handled easily with only a few isolation of intermediates. The process is explained below:

(1) The fluorochlorocyclopropane (I) is prepared by treating an olefin (II) represented by the following formula:

$$CH_2=CR^1\text{-}R^2 \quad (II)$$

with dichlorofluoromethane in the presence of a base.

The base can be an inorganic base, e.g., alkali metal hydroxide, or an organic base, e.g., 1 to 5C-alcoholate or alkali metal or alkaline earth metal, alkylalkali metal, arylalkali metal, or the like capable of producing fluorochlorocarbene by reacting with dichlorofluoromethane.

The reaction is usually carried out in a solvent. The solvent is preferably that inert to the starting material, product, or fluorochlorocarbene (e.g., that having no reactive double bond nor halogen) and causing less side reaction (e.g., polymerization of the starting material or product), for example, industrial solvents of hydrocarbon or ether series. This reaction is not disturbed by water. Excess starting olefin or dichlorofluoromethane can play a role of solvent. The reaction is usually carried out at between $-50°$ C. and $50°$ C., preferably $-20°$ C. and $40°$ C. for 1 to 10 hours time.

In a typical case, a solution of dichlorofluoromethane (2 to 3 molar equivalents) and the olefin (II) (1 molar equivalent) in water (0.8 to 2 weights) containing sodium or potassium hydroxide (2 to 10 molar equivalents) is stirred for 3 to 5 hours to give the objective fluorochlorocyclopropane (I) in up to 90% yield.

So-called crown ethers, phase transfers reagents in two-phase reaction (e.g., tetra-lower alkylammonium halide, methyl-trilower alkyl-ammonium halide), or the like promotes the reaction.

Fluorochlorocyclopropanes (I) are useful as intermediates for chemicals (e.g., fluoropolymers, fluoroacrylic acid, medicines).

(2) For example, fluorochlorocyclopropane (I) is heated at between $60°$ C. and $200°$ C., preferably $80°$ C. and $160°$ C., in a solvent to supposedly give intermediary fluororchloroporpene (III) usually for 30 minutes to 10 hours.

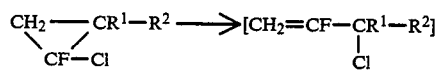

The solvent is water or an inert organic solvent (e.g., hydrocarbon, halohydrocarbon, alcohol, aromatic base).

(3) The fluorochloropropene (III) reacts with alcohol ($R^3OH$: $R^3$ is 1 to 4C alkyl) to give an acetal or aminal or acrolein or an ortho ester of acrylic acid (IV). An acid scavenger (e.g., aromatic base, alkylamine) improves the yield.

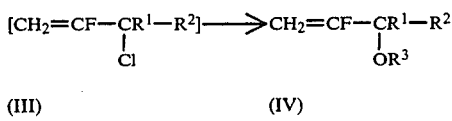

(III)    (IV)

(4) The acetal or aminal or acrolein or thioester or ortho ester of acrylic acid (IV) adds halogen (e.g., bromine) to the double bond. For example, compound (IV) is dissovled in a halohydrocarbon solvent and mixed with bromine to give dibromofluoropropane (V) which is heated with a base (e.g., DBU) to give bromofluoropropene (VI).

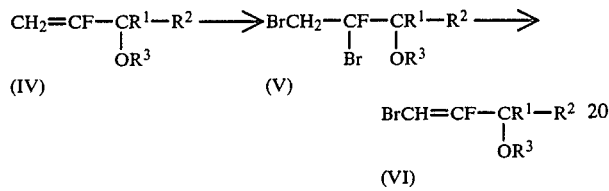

(IV)    (V)

(VI)

(5) By thermal decomposition of fluorochlorocyclopropane (I), the corresponding carbonyl compound (IVa) can be produced.

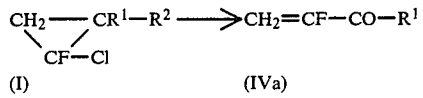

(I)    (IVa)

(6) The acetal or aminal or acrolein or an ortho ester of acrylic acid (IV), dibromofluoropropane (V), or bromofluoropropane (VI), is hydrolyzed with acid to give a carbonyl compound (IVa to VIa). An aqueous reaction is promoted with a surface active reagent.

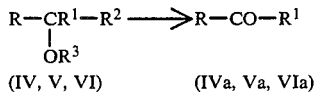

(IV, V, VI)    (IVa, Va, VIa)

(wherein R is $CH_2=CF-$, $BrCH=CF-$, or $BrCH_2-CFBr-$)

(7) An acetal or aminal (IV), dibromofluoropropane (V), or bromofluoropropene (VI), i.e., where $R^1$ is hydrogen, can be oxidized as follows to give an ester, amide, or thioester of propionic acid (IVa to VIa) leaving a double bond, if any, intact.

R-CHR²-OR³ (IV to VI)→R-COR² (IVa to VIa)

This oxidation is carried out with an inorganic or organic peracid (e.g., persulfuric acid, periodic acid, nitrogen dioxide, percarboxylic acids), molecular halogen (e.g., chlorine, bromine), hypohalite or its precursor (e.g., hypohalogenous acid, its salt or ester, N-haloamide, N-haloimide), organic peroxide, hydrogen peroxide, or the like, or salts thereof, preferably at an amount of 1 to 10 molar equivalents, in a solvent at between −20° and 100° C., preferably 40° and 85° C., for 10 minutes to 10 hours, preferably 1 to 5 hours. Aldehyde, if resulting from acetal hydrolysis (e.g., with acid contaminant) in the medium, is oxidized to give carboxylic acid.

In a typical reaction, persulfuric acid or Caro's acid (1 to 10 molar equivalents) is added to a solution of the starting acetal in lower alkanol (3 to 5 parts by weight), and the mixture is warmed at between room temperature and 80° C. for 1 to 5 hours.

A typical use of the product is as follows: Namely, the propionate (VIa) is combined with alkyl thioglycolate to give carboxymethylfluoroacrylate (VII) which is hydrolyzed to give (VIII) which is then treated with 7-amino-3-substituted methyl-3-cephem-4-carboxylate in a usual manner to afford an antibacterial cephalosporin (IX).

(VIa)

(VIII)

(VIII)

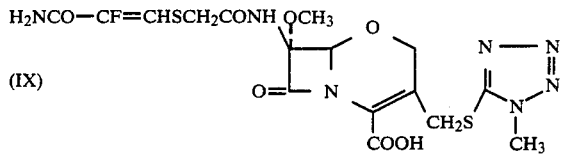

(IX)

The solvent for above reactions is an industrial solvent of a series hydrocarbon (e.g., pentane, hexane, octane, benzene, toluene, xylene), halogenated hydrocarbon (e.g., dichloromethane, chloroform, carbon tetrachloride, dichloroethane, trichloroethane, chlorobenzene), ether (e.g., diethyl ether, methyl isobutyl ether, dioxane, tetrahydrofuran), ketone (e.g., acetone, methyl ethyl kentone, cyclohexanone), ester (e.g., ethyl acetate, isobutyl acetate, methyl benzoate), nitrohydrocarbon (e.g., nitromethane, nitrobenzene), nitrile (e.g., acetonitrile, benzonitrile), amide (e.g., formamide, acetamide, dimethylformamide, dimethylacetamide, hexamethylphosphorotriamide), alcohol (e.g., methaol, ethanol, propanol, hexanol, octanol, benzylalcohol), water, or the like or a mixture of these.

Work up of above reactions includes removing (e.g., by extracting, evaporating, washing, concentrating, precipitating, filtering, drying) of contaminants (e.g., unreacted starting material, by-product, solvent) and purification (e.g., by adsorbing, eluting, distilling, precipitating, separating, chromatographying) to isolate the objective product in a conventional manner.

Following examples and experiments illustrate this invention.

Physical constants of the products in which IR shows $cm^{-1}$ value and NMR shows δ value and J value of coupling constants in Hz scale. The physical constants of the products are listed in the Tables 3 to 7.

The method for work up is usually as follows: the reaction mixture is, if necessary, diluted with water and dichloromethane or ethyl acetate, separating organic phase is taken up, washed with water, dried, and concentrated to leave residue. If required after silica gel chromatography, the residue is purified by crystallizing, precipitating, filtrating, etc., to give the product. Physical constants of the products are same with the samples produced by other route.

Abbreviations are as follows:

eq=molar equivalents per mole of the starting material, rt=room temperature, and wt=parts by weight per weight of the starting material.

EXAMPLE 1

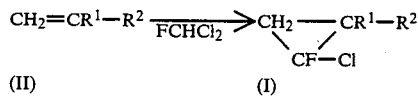

(II)  (I)

To a solution of an olefin (II) in a solvent are added a base and dichlorofluoromethane, and the mixture is stirred for given time at given temperature, if required in the presence of an additive reagent.

The reaction mixture is washed with water and aqueous sodium hydrogen carbonate, dried over magnesium sulfate and concentrated. The residue is distilled in vacuum to afford the corresponding fluorochlorocyclopropane (I). The reaction conditions are listed on Table 1.

TABLE 1

| | | | | | | | |
|---|---|---|---|---|---|---|---|
| $R^1$ | $R^2$ | $FCHCl_2$ | base | Solvent | temp. | time | reagent |
| $OC_2H_5$ | H | 20 eq | KOH 28 eq | $H_2O$ 0.8 wt | rt | 5 hr | $(n-C_4H_9)_4NBr$ 0.1 wt |
| $OC_4H_9-n$ | H | 20 | KOH 20 | $H_2O$ 0.75 | rt | 4 | Aldrich Adogen 464 0.17 wt |
| $OC_4H_9-i$ | H | 22 | KOH 8.8 | $H_2O$ 2 | 0 | 5.0 | 0.6 wt 18-crown-6 |
| $OC_2H_5$ | $OC_2H_5$ | 28 | $KOC_4H_9-t$ 1.5 | $C_6H_{14}$ 15 | $-20°$ C. | 1.5 | — |
| $OC_2H_5$ | $OC_2H_5$ | 28 | $C_4H_9Li$ 1.5 | $C_6H_{14}$ 15 | $-10$ | 1.5 | — |
| $SCH_3$ | $N(CH_3)_2$ | 25 | $C_4H_9Li$ 20 | $(C_2H_5)_2O$ 10 | $-78$ | 1.0 | — |

EXAMPLE 2

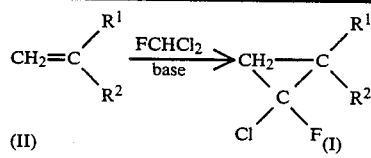

$$CH_2=CF-COR^1$$

(IVa)

To a solvent heated in vacuum is added fluorochlorocyclopropane (I), and evaporating carbonyl compound (IVa) is collected by condensing. The reaction conditions are given on Table 2.

TABLE 2

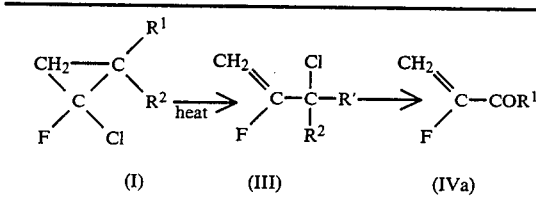

| $R^1$ | $R^2$ | Solvent | Temp. (°C.) | mmHg | Yield (%) |
|---|---|---|---|---|---|
| $OC_2H_5$ | $OC_2H_5$ | Parafin | 170 | 650 | 47 |
| " | " | $C_6H_4Cl_2$ | 150 | 160 | 48 |
| " | " | $C_6H_3Cl_3$ | 140 | 360 | 82 |

EXAMPLE 3

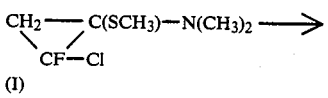

(I)

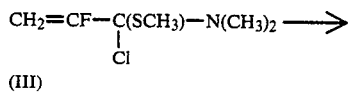

(III)

$$CH_2=CF-CO(SCH_3)$$ (IVa)

A suspension of 1-chloro-1-fluoro-2-dimethylamino-2-methylthiocyclopropane (238 mg) and hydroquinone (40 mg) in aqueous 0.015M-sodium dodecylsulfate is stirred for 1 hour at 80° and 90° C. The reaction mixture is poured into ice water and extracted with ether. The extract solution is washed with water, dried, and concentrated to give methyl α-fluorothiolacrylate (200 mg).

EXAMPLE 4

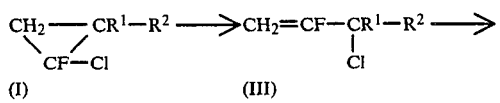

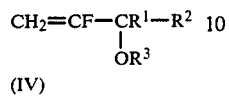

(1) $R^1 = H$, $R^2 = OC_4H_9\text{-n}$, $R^3 = C_4H_9\text{-n}$.

A mixture of 1-chloro-1-fluoro-2-n-butoxycyclopropane (42 g), pyridine (24 ml), and n-butanol (150 ml) is refluxed for 17 hours. The reaction mixture is poured onto aqueous potassium carbonate and extracted with ether. The extract is washed with water, dried, and concentrated. The residue is distilled in vacuum to give α-fluoroacrolein di-n-butylacetal. bp(12 mmHg): 83°–85° C.

(2) $R^1 = R^2 = C_2H_5O$, $R^3 = C_2H_5$.

A solution of 1-chloro-1-fluoro-2,2-diethoxycyclopropane (5 g) in a mixture of benzene (25 ml), ethanol (2.38 ml), and pyridine (2.65 ml) is refluxed for 1 hour. The reaction mixture is filtered to remove separated salt and concentrated in vacuum. The residue is distilled to give ortho-ethyl ester of α-fluoroacrylic acid (3.7 g). Yield: 70.3%. bp(40 mmHg): 77° C.

Experiment 1 (Addition of bromine to an ether (IIIb))

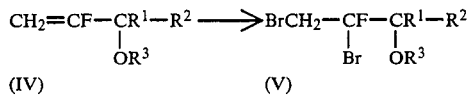

To a solution of Compound (IV) in 8 volumes of carbon tetrachloride is added bromine (1.1 eq.) under ice cooling, and the mixture is stirred at 0° C. to 30° C. for 10 minutes to 4 hours. The reaction mixture is washed with water, aqueous sodium thiosulfate, and water, dried, and concentrated to give the corresponding dibromo compound (V). Similarly, the compounds on Table 5 can also be produced.

(1) $R^1 = H$, $R^2 = OC_4H_9\text{-n}$, $R^3 = C_4H_9\text{-n}$: bp(4mmHg): 96°–98° C.

(2) $R^1 = H$, $R^2 = OC_4H_9\text{-i}$, $R^3 = C_4H_9\text{-i}$: $^{19}F$ NMR: +50.8 (ddd, J=20, 17, 4 Hz).

(3) $R^1 = R^2 = OC_2H_5$, $R^3 = C_2H_5$: bp(15 mmHg): 83°–85° C.

Experiment 2 (Addition of bromine to Ketone (IIIa))

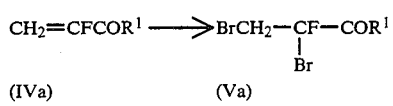

The reaction of Experiment 1 is repeated at 80° C. to give the corresponding dibromide (Va) wherein $R^1 = OC_2H_5$ or $R^1 = OC_4H_9\text{-n}$. Similarly, the compounds on Table 5 can also be produced.

Experiment 3 (Dehydrobromination of bromides)

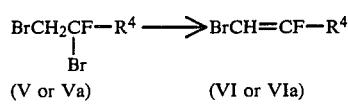

The bromofluorovinyl compound (VI or VIa) is obtained by refluxing a solution of the corresponding dibromide (V or Va) (1 part by weight) in benzene (5 to 20 parts by weight) containing DBU (0.1 to 2 molar equivalents) for 0.5 to 5 hours in 50 to 85% yield. The products are listed on Table 6.

$R^4 = CH(OC_4H_9\text{-n})$; $R^4 = CH(OC_4H_9\text{-i})$; $R^4 = COOCH_3$; $R^4 = COOC_2H_5$; $R^4 = COOC_4H_9\text{-n}$; $R^4 = COOC_4H_9\text{-i}$.

Experiment 4 (Oxidation with peracetic acid)

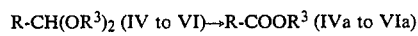

A solution of acetal (IV to VI) and peracetic acid (1 equivalent) in ethyl acetate (1 part) is stirred at 60° C. for 2 hours. After cooling, excess reagent is reduced. After neutralizing with sodium acetate, the solvent is evaporated to give carboxylic acid (IVa to VIa) ($R^3 = H$). By treating this with diazoethane, the corresponding ethyl ester is obtained.

Experiment 5 (Oxidation with NBS)

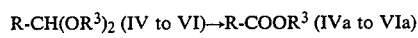

To a solution of acetal (IV to VI) in carbon tetrachloride (16 parts) is added N-bromosuccinimide (1.5 equivalents), and the mixture is refluxed for 3 hours. The reaction mixture is washed with water, dried, and concentrated. The residue is distilled in vacuum to give the corresponding carboxylic acid ester (IVa to VIa).

Experiment 6 (Oxidation with Caro's acid)

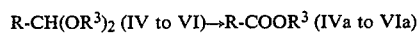

A solution of acetal (IV to VI) and Caro's acid (6.8 equivalents) in n-butanol (3.1 part) is stirred at room temperature for 3 hours and at 50° C. to 60° C. for 1 hour. The reaction mixture is poured onto ice water and extracted with dichloromethane. The extract is washed with water, dried, and concentrated in vacuum. The residue is distilled in vacuum to give the corresponding carboxylic acid ester (IVa to VIa) in about 90% yield.

By the methods of Examples 1 to 3, compounds of Table 7 are produced from the corresponding acetals.

TABLE 3

Physical constants of $$\text{CH}_2\underset{\underset{F}{C}\underset{Cl}{\diagdown}}{\overset{\overset{R^1}{\diagup}}{\overline{\phantom{CC}}}C\overset{R^1}{\underset{R^2}{\diagdown}}} \quad (I)$$

| No. | R¹ | R² | bp(°C.) (mmHg) | IR ν(film) cm⁻¹. | NMR δ (CDCl₃) ppm |
|---|---|---|---|---|---|
| 1 | OC₂H₅ | H | — | 1170, 1130. | 1.22 (t, J=7Hz, 3H), 1.25–1.85 (m, 2H), 3.3–3.85 (m, 3H). |
| 2 | OC₄H₉—n | H | 43–45(7) | 1170, 1125, 1080. | 0.91 (t, J=7Hz, 3H), 1.15–1.85 (m, 6H), 3.3–3.8 (m, 3H). |
| 3 | OC₄H₉—i | H | 60(47) | 3100. | 0.92 (d, J=6Hz, 6H), 1.1–2.2 (m, 3H), 3.2–3.9 (m, 3H). |
| 4 | OC₂H₅ | OC₂H₅ | 54–57(20) | 1150, 1080, 1030 (CHCl₃). | 1.24 (t, J=7.5Hz, 6H), 1.17–1.88 (m, 2H), 3.78 (q, J=7.5Hz, 4H). |
| 5 | N(CH₃)₂ | SCH₃ | — | 1270, 1105. | 1.35–1.85 (m, 2H), 2.24 (s, 3H) 2.33 (s, 6H). |
| 6 | SCH₃ | N(CH₃)₂ | — | 1080. | 1.40–1.88 (m, 2H), 2.25 (s, 3H), 2.37 (s, 6H). |

TABLE 4

Physical constants of $CH_2=CF-R$ (IVa)

| No. | R | bp(°C.) (mmHg) | IR ν(film) dm⁻¹. | NMR δ (CDCl₃) ppm |
|---|---|---|---|---|
| 1 | —CH(OC₂H₅)₂ | — | | ¹⁹F NMR δ +50.6 (ddd, J=4;17;49Hz). |
| 2 | —CH(OC₄H₉—n)₂ | 83–85(12) | 1680, 1115, 1070. | 0.93 (t, J=7Hz, 6H), 1.2–1.8 (m, 8H), 3.35–3.75 (m, 4H), 4.80 (dd, J=50;3Hz, 1H), 4.80 (dd, J=17;3Hz, 1H), 4.92 (d, J=3Hz, 1H). |
| 3 | —CH(OC₄H₉—i)₂ | 80–82(20) | 1680. | 0.92 (d, J=6Hz, 12H), 1.3–2.1 (m, 2H), 3.0–3.5 (m, 4H), 4.73 (dd, J=17;3Hz, 1H), 4.78 (dd, J=49;3Hz, 1H), 4.90 (br, 1H). |
| 4 | —C(OC₂H₅)₃ | 73–76(40) | 1678, 1097*. | 1.20 (t, J=7.5Hz, 9H), 3.54 (q, J=7.5Hz, 6H), 4.94 (dd, J=16.5; 2.3Hz, 1H), 4.99 (dd, J=48;2.3Hz, 1H). |
| 5 | —COOC₂H₅ | 45(360) | 1730, 1660, 1325, 1175, 1100(CHCl₃). | 1.32 (t, J=7.5Hz, 3H), 4.29 (q, J=7.5Hz, 2H), 5.29 (dd, J=13.5; 3Hz, 1H), 5.65 (dd, J=44;3Hz, 1H) |
| 6 | —COOC₄H₉—n | 51–53(15) | 1730, 1650. | 0.8–2.0 (m, 5H), 4.25 (t, J=7Hz, 2H), 5.30 (dd, J=13.2;3Hz, 1H), 5.67 (dd, J=43.3; 3Hz, 1H) |
| 7 | —COOC₄H₉—i | | | |
| 8 | —COSCH₃ | — | — | 2.35 (s, 3H), 5.53 (dd, J=45; 4Hz, 1H), 5.06 (dd, J=15;4Hz, 1H). |

*(CHCl₃)

TABLE 5

Physical constants of $$\text{Br}-\text{CH}_2-\underset{\underset{Br}{|}}{CF}-R \quad (V \text{ or } Va)$$

| No. | R | bp(°C.) (mmHg) | IR ν(film) cm⁻¹ | NMR δ (CDCl₃) ppm |
|---|---|---|---|---|
| 1 | —CH(OC₄H₉—n)₂ | 115(3) | 1190. | 0.91 (t, J=7Hz, 6H), 1.15–1.75 (m, 8H), 3.4–3.9 (m, 4H), 3.97 (d, J=17Hz, 1H), 4.02 (d, J=20Hz, 1H), 4.67 (d, J=4Hz, 1H). |
| 2 | —CH(OC₄H₉—i)₂ | — | — | 0.92 (d, J=6Hz, 12H), 1.5–2.2 (m, 2H), 3.05–3.6 (m, 4H), 3.90 (d, J=17Hz, 1H), 3.93 (d, J=20Hz, 1H), 4.65 (d, J=4Hz, 1H). |
| 3 | —C(OC₂H₅)₃ | | | |
| 4 | —COOC₂H₅ | 83–85(15) | 1765, 1310, 1043(CHCl₃). | 1.37 (t, J=7.5Hz, 3H), 3.9–4.5 (m, 2H), 4.40 (q, J=7.5Hz, 2H). |

TABLE 6

Physical constants of Br—CH=CF—R    (VI or VIa)

| No. | R | bp(°C.) (mmHg) | IR ν(film) cm$^{-1}$. | NMR δ (CDCl$_3$) ppm |
|---|---|---|---|---|
| 1 | —CH(OC$_2$H$_5$)$_2$ | | 1670, 1100, 1070. | 0.91 (t, J=7Hz, 6H), 1.15–1.75 (m, 8H), 3.35–3.75 (m, 4H), 4.97 (s, 1H), 5.94 (d, J=28Hz, 1H). |
| 2 | —CH(OC$_4$H$_9$—n)$_2$ | 96–98(4) | | |
| 3 | —CH(OC$_4$H$_9$—i)$_2$ | 98–105(6) | 3120, 1675. | 0.93 (d, J=6Hz, 12H), 1.4–2.1 (m, 2H), 3.0–3.5 (m, 4H), 4.93 (t, J=1Hz, 1H), 5.87 (dd, J=27; 1Hz, 1H). |
| 4 | —COOCH$_3$ | — | 1735, 1640. | 3.83 (s, 3H), 6.93 (d, J=24Hz, 1H). |
| 5 | —COOC$_2$H$_5$ | 80(40) | 1730, 1645, 1310, 1095*. | 1.33 (t, J=7.5Hz, 3H), 4.31 (q, J=7.5Hz, 2H), 6.93 (d, J=24Hz, 1H) |
| 6 | —COOC$_4$H$_9$—n | 73–75(5) | 1735, 1643. | 0.8–2.0 (m, 7H), 4.23 (t, J=6 Hz, 2H), 6.87 (d, J=24Hz, 1H). |
| 7 | —COOC$_4$H$_9$—i | 110(45) | 3110. | 0.97 (d, J=6Hz, 6H), 1.5–2.3 (m, 1H), 4.00 (d, J=6Hz, 2H), 6.90 (d, J=24Hz, 1H). |

*(CHCl$_3$)

TABLE 7

Physical constants of R—COOR$^3$    (IVa to VIa)

| No. | R | R$^3$ | bp(°C.) (mmHg) | IR ν (film): cm$^{-1}$. | NMR δ (CDCl$_3$); ppm |
|---|---|---|---|---|---|
| 1 | CH$_2$=CF— | H | — | — | 5.20 (dd, J=14;3Hz, 1H), 5.50 (dd, J=43;3Hz, 1H)(CH$_3$COOH + CH$_3$COOC$_2$H$_5$). |
| 2 | CH$_2$=CF— | C$_2$H$_5$ | 45(360) | 1730, 1660, 1325, 1175, 1100(CHCl$_3$). | 1.32 (t, J=7.5Hz, 3H), 4.29 (q, J=7.5Hz, 2H), 5.29 (dd, J=13.5; 3Hz, 1H), 5.65 (dd, J=44;3Hz, 1H). |
| 3 | CH$_2$=CF— | C$_4$H$_9$—n | 53(15) | 1730,1650. | 0.8–2.0 (m, 5H), 4.25 (t, J=7Hz, 2H), 5.30 (dd, J=13.2;3Hz, 1H), 5.67 (dd, J=43.3;3Hz, 1H). |
| 4 | CH$_2$=CF— | C$_4$H$_9$—i | — | — | — |
| 5 | BrCH=CF— | H | — | — | 6.93 (d, J=24Hz, 1H). |
| 6 | BrCH=CF— | CH$_3$ | — | 1735, 1640. | 3.83 (s, 3H), 6.93 (d, J=24Hz, 1H). |
| 7 | BrCH=CF— | C$_2$H$_5$ | 80(40) | 1730,1645, 1310, 1095 (CHCl$_3$). | 1.33 (t, J=7.5Hz, 3H), 4.31 (q, J=7.5Hz, 2H), 6.93 (d, J=24Hz, 1H). |
| 8 | BrCH=CF— | C$_4$H$_9$—n | 75(5) | 1735, 1643. | 0.8–2.0 (m, 7H), 4.23 (t, J=6Hz, 2H), 6.87 (d, J=24Hz, 1H). |
| 9 | BrCH=CF— | C$_4$H$_9$—i | 110(45) | 3110. | 0.97 (d, J=6Hz, 6H), 1.5–2.3 (m, 1H), 4.00 (d, J=6Hz, 2H), 6.90 (d, J=24Hz, 1H). |
| 10 | BrCH$_2$CF—Br | C$_2$H$_5$ | 85(15) | 1765, 1310, 1043(CHCl$_3$). | 1.37 (t, J=7.5Hz, 3H), 3.9–4.52(m, 2H), 4.40 (q, J=7.5Hz, 2H). |

What we claim is:

1. A fluorochlorocyclopropane compound represented by the following formula:

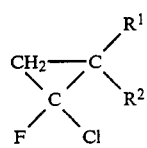

wherein R$^1$ is, 1 to 8C alkylamino, alkoxy, or alkylthio; and R$^2$ is, 1 to 8C alkylamino, alkoxy, or alkylthio.

2. A fluorochlorocyclopropane compound according to claim 1 wherein R$^2$ is a 1 to 8C alkylamino.

3. A fluorochlorocyclopropane compound according to claim 1 wherein R$^2$ is a 1 to 8C alkoxy.

4. A fluorochlorocyclopropane compound according to claim 1 wherein R$^1$ is a 1 to 8C alkylthio and R$^2$ is a 1 to 8C alkylamino.

5. A fluorochlorocyclopropane compound according to claim 1 wherein R$^1$ is 1 to 8C alkoxy and R$^2$ is 1 to 8C alkoxy.

* * * * *